United States Patent
Nakayama

(10) Patent No.: US 9,279,790 B2
(45) Date of Patent: Mar. 8, 2016

(54) ANALYSIS METHOD FOR DYE FOR ORGANIC SOLAR CELL AND PURIFICATION METHOD THEREFOR

(71) Applicant: SHIMADZU CORPORATION, Kyoto-shi, Kyoto (JP)

(72) Inventor: Daisuke Nakayama, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 74 days.

(21) Appl. No.: 14/349,760

(22) PCT Filed: Dec. 28, 2012

(86) PCT No.: PCT/JP2012/084120
§ 371 (c)(1),
(2) Date: Apr. 4, 2014

(87) PCT Pub. No.: WO2013/111512
PCT Pub. Date: Aug. 1, 2013

(65) Prior Publication Data
US 2014/0245818 A1   Sep. 4, 2014

(30) Foreign Application Priority Data

Jan. 24, 2012 (JP) .................. 2012-011633

(51) Int. Cl.
| | |
|---|---|
| *G01N 30/02* | (2006.01) |
| *G01N 30/80* | (2006.01) |
| *C09B 57/10* | (2006.01) |
| *G01N 30/88* | (2006.01) |
| *H01L 51/00* | (2006.01) |
| *H01G 9/20* | (2006.01) |

(52) U.S. Cl.
CPC .............. *G01N 30/80* (2013.01); *C09B 57/10* (2013.01); *G01N 30/88* (2013.01); *H01L 51/0025* (2013.01); *H01L 51/0086* (2013.01); *G01N 2030/027* (2013.01); *G01N 2030/8809* (2013.01); *H01G 9/2059* (2013.01); *Y02E 10/549* (2013.01)

(58) Field of Classification Search
None
See application file for complete search history.

(56) References Cited

U.S. PATENT DOCUMENTS

2010/0275391 A1    11/2010   Fuhrmann et al.

FOREIGN PATENT DOCUMENTS

| JP | 2010-265236 A | 11/2010 |
|---|---|---|
| JP | 2011-505651 A | 2/2011 |

OTHER PUBLICATIONS

Strege, M.A., Hydrophilic Interaction Chromatography-Electrospray Mass Spectrometry Analysis of Polar Compounds for Natural Product Drug Discovery, 1998, Analytical Chemistry, vol. 70, pp. 2439-2445.*
International Search Report for PCT/JP2012/084120, Mailing Date of Feb. 26, 2013.

* cited by examiner

*Primary Examiner* — Robert Xu
(74) *Attorney, Agent, or Firm* — Westerman, Hattori, Daniels & Adrian, LLP

(57) ABSTRACT

This analysis method includes: subjecting a sample solution of a dye-containing sample in an organic solvent to normal-phase liquid chromatography to separate the sample solution and detect separated components. The normal-phase liquid chromatography involves (B1) using a separation column filled with a column packing material which is prepared by modifying a base material with a polar modifying group, and (B2) using as an eluent a polar organic solvent containing an acid.

7 Claims, 3 Drawing Sheets

N3 Dye

Isomer of N3 Dye

ANALYSIS METHOD FOR DYE FOR ORGANIC SOLAR CELL AND PURIFICATION METHOD THEREFOR

TECHNICAL FIELD

The present invention relates to an analysis method for dyes for organic solar cells, and a preparative purification method therefor, and more particularly to, for example, analysis for assay and quality control, and preparative purification in the final stage of a manufacturing process.

BACKGROUND ART

Dyes for organic solar cells are molecular dyes used as a sensitizer in dye-sensitized solar cells. As a method for purifying such molecular dyes, proposed has been a method for purifying a dye by adding an alkali to a sample containing a molecular dye of which the purity fails to reach a desired level, to convert the dye into aqueous form, and fractionating the dye through reversed-phase chromatography (Patent Document 1).

PRIOR ART DOCUMENTS

Patent Documents

Patent Document 1: Japanese Translation of PCT International Application No. 2011-505651

SUMMARY OF THE INVENTION

Problems to be Solved by the Invention

Many dyes for organic solar cells have low stability to water, which has caused a problem that the dyes deteriorated after purification in reversed-phase separation methods using water.

Accordingly, an object of the present invention is to achieve analysis or purification of dyes for organic solar cells, without deteriorating the dyes.

Solutions to the Problems

The present invention aims at analyzing dyes for organic solar cells or separating them for preparative purification in a water-free separation system, and uses normal-phase chromatography which is a water-free high separation method. The dyes for organic solar cells to be analyzed in the present invention are acidic compounds having one or more acidic groups such as a carboxyl group. When the normal-phase method is used, the polarity of a column packing material, i.e., a stationary phase, is higher than that of a mobile phase in normal conditions, which has caused a problem that the adsorption of the dye to the column packing material is too strong to obtain sufficient separation.

Therefore, in the present invention, the conditions of normal-phase chromatography are controlled as follows to separate the dye which is an acidic compound.

The base material of the column packing material is modified with a polar group. The type of the polar modifying group is selected according to the degree of adsorption of the dye which is a sample.

As an eluent, one containing a polar organic solvent and an acid is used. The ratio of the solvent, and the type and the ratio of the acid in the eluent are controlled according to the degree of adsorption of the sample.

Specifically, the analysis method of the present invention is a method for analyzing a dye for dye-sensitized solar cells in a sample containing the dye, the method comprising the steps of:
  (A) providing a sample solution of the sample in an organic solvent;
  (B) separating the sample solution by normal-phase liquid chromatography; and
  (C) detecting separated components.
The normal-phase liquid chromatography involves:
  (B1) using a separation column filled with a column packing material which is prepared by modifying a base material with a polar modifying group, and
  (B2) using as an eluent a polar organic solvent containing an acid.

This analysis method further comprises a preparative purification process by providing the step of recovering a target dye based on a detection result, after the detection step (C), for preparative purification of the dye.

The target dye is a dye for dye-sensitized solar cells, and is a metal complex having one or more aromatic heterocyclic ligands.

The aromatic heterocyclic ligand in the metal complex is a polypyridyl derivative or a porphyrin derivative, and contains one or more nitrogen atoms bonded to a metal. The metal is Mg, Ca, Sr, Ba, Sc, Y, La, Ce, Pr, Nd, Sm, Eu, Gd, Tb, Dy, Ho, Er, Tm, Yb, Lu, Ti, Zr, Hf, V, Nb, Ta, Th, Cr, Mo, W, Mn, Tc, Re, Fe, Ru, Os, Co, Rh, Ir, Ni, Pd, Pt, Cu, Ag, Au, Zn, Cd, Hg, Al, Ga, In, Tl, Si, Ge, Sn, Pb, As, Sb, or Bi; and is preferably Ru, Os, or Zn among them.

In addition, this dye has one or more acidic groups. The acidic group is a carboxyl group, a sulfonyl group, or a phosphoryl group, and preferably a carboxyl group. Some or all of the acidic groups form salts with monovalent cations such as tetraalkylammonium, ammonium, sodium, or potassium, depending on the condition.

The modifying group of the column packing material is preferably a hydroxyl group, a cyano group, or an amino group. Either one modifying group may be used or two or more modifying groups may be used together to modify one column packing material. These modifying groups are selected based on the degree of adsorption of the dye.

In general, the interaction of the sample to the column packing material increases in the order of the following modifying groups of the column packing material: amino group>hydroxyl group>cyano group. For this, roughly, a cyano group and a hydroxyl group with weaker interaction are used as a modifying group of the column packing material for dyes with strong adsorption; and an amino group and a hydroxyl group with stronger interaction are used as a modifying group of the column packing material for dyes with weak adsorption.

In fact, an amino group as a modifying group of the column packing material may not be appropriate to use due to strong interaction with the carboxyl group of the dye.

Organic solvents including 1 to 8 carbon (C) atoms or a mixture thereof is used as a solvent for the eluent. Preferred examples of such organic solvents include nitriles such as acetonitrile, alcohols such as methanol, cyclic ethers such as tetrahydrofuran, ethers such as diethyl ether, ketones such as acetone, halocarbons such as dichloromethane, benzene derivatives such as toluene, esters such as ethyl acetate, and hydrocarbons such as hexane, and mixtures containing these solvents.

In general, elution is accelerated using high content of a solvent with high polarity. The solvent is selected by actual analysis of the dye through the liquid chromatography using the above solvent and subsequent confirmation of the separation state.

Strong interaction of the acidic group contained in the dye with the column packing material often results in insufficient column separation only with the above solvent. Accordingly, the interaction of the acidic group of the dye with the column packing material is suppressed by addition of one or more acids to the solvent to increase the performance of separation. The acid to be added is/are organic acids including 1 to 4 C atoms, preferably carboxylic acids such as formic acid and trifluoroacetic acid, sulfonic acids, and phosphonic acids. Organic acids having two or more acidic groups, such as oxalic acid, may be added. The salts of these acids may be added. Either one acid may be added or two or more acids may be added together to the eluent. The acid or the salt thereof is also selected based on the degree of adsorption of the dye. For example, more carboxyl groups contained in the dye require selection of the acid with higher acidity to be added to the solvent.

When the present invention is performed as a purification method, the solvent must be removed after fractionation, and thus, the volatility of the solvent is preferably higher in terms of solvent removal. For this reason, the acid to be added to the solvent preferably has/have less carbon atoms. Accordingly, formic acid is first used to check the degree of separation and the peak shape, and trifluoroacetic acid is tested in consideration of these. Finally, based on the data actually obtained, and the acid to be added to the solvent and the concentration of the acid are determined.

Depending on the strength of the interaction of the dye with the column packing material, 0.01% to 5% of the acid is added to the solvent. When the interaction is strong, a high level of the acid is added. When the interaction is weak, a low level of the acid may be added but high level of the acid may also be added.

The normal-phase liquid chromatography is preferably performed using a high-resolution high-speed liquid chromatograph.

Effects of the Invention

In the present invention, even with normal-phase chromatography, sufficient separation can be obtained by using a modified column packing material and adding the acid to the eluent to control the adsorptive power of the dye to the packing material. As a result, unlike conventional separation methods using reversed-phase chromatography, the present invention uses normal-phase chromatography, and thus, need not to use water in the eluent, which prevents the dye from being deteriorated by water when the dye is unstable in water. Application of the present invention to the preparative purification method can prevent deterioration of the dye after purification, and application of the present invention to the analysis method can prevent deterioration of the dye during the analysis and achieve stable analysis.

MODE FOR CARRYING OUT THE INVENTION

Dyes are synthesized by a manufacturing process, purified by a fractionation system, and supplied to the market after the purification. However, the purity of many dyes after the purification is not sufficient as dyes used for organic solar cells. In particular, isomers are not removed well from many dyes. Higher purity is preferred for use in organic solar cells.

The preparative purification method of the present invention can be applied as a method for increasing the purity of dyes that contain such impurities and are supplied to the market, to provide dyes suitable for use in organic solar cells.

Dyes synthesized by a manufacturing process contain impurities, and thus, require preparative purification before provided to the market. The preparative purification method of the present invention can also be applied to the preparative purification step before the dyes are provided to the market.

As a sample of an example, N3 dye used in organic solar cells is tested for separation analysis with a high-speed liquid chromatograph as illustrated below. The preparative purification and the analysis with a liquid chromatograph are common in separation process and detection and different only in whether to fractionate or not based on the result of the detection.

Although an analysis method is shown as an example, the analysis conditions can also be applied as they are to preparative chromatography which is a subsequent example.

Figure 1A:
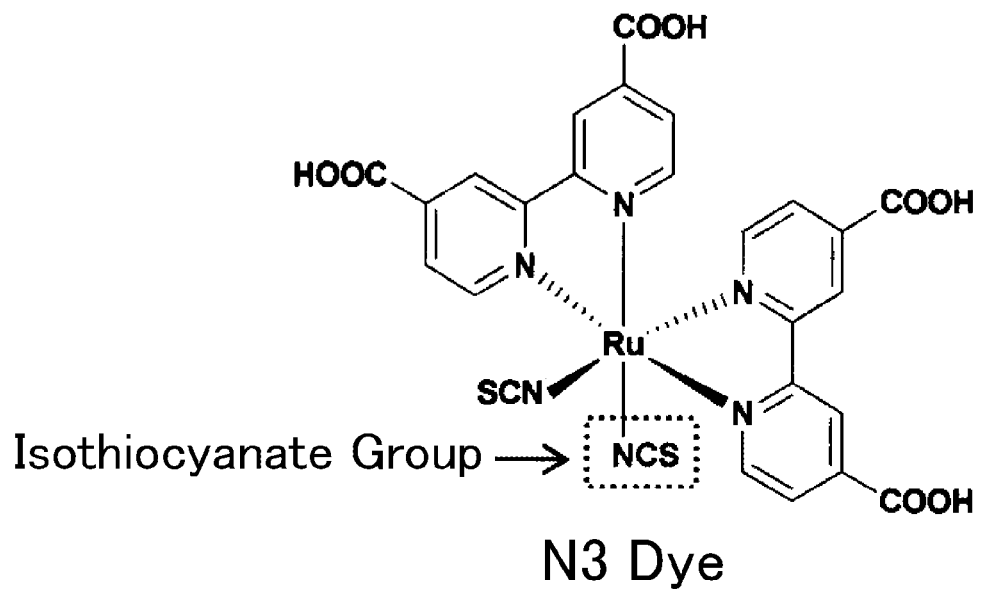
FIG. 1A is a chemical formula showing N3 dye which is a sample used in an analysis method of an example.
Figure 1B:
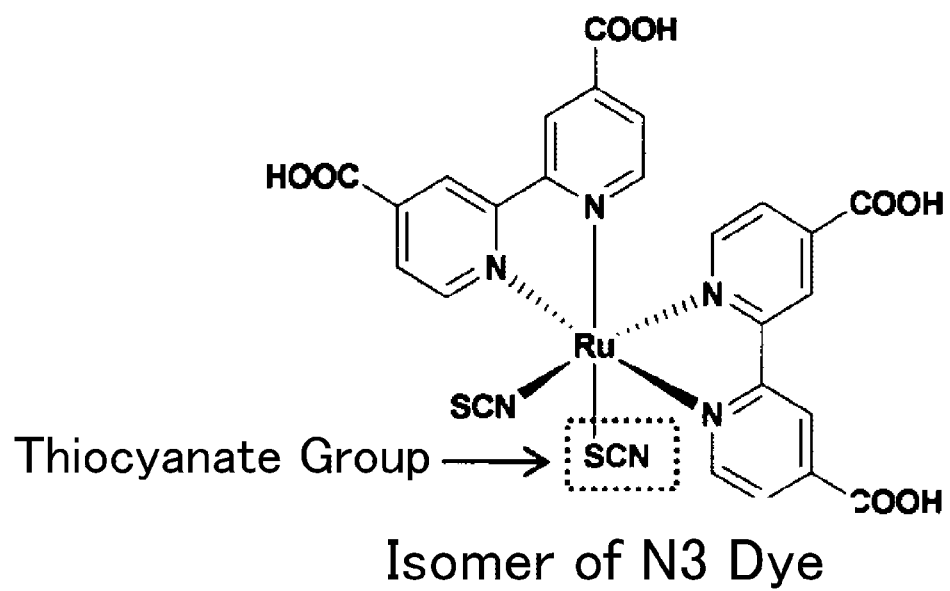
FIG. 1B is a chemical formula showing an isomer of N3 dye.

The structural formula of N3 dye is shown in FIG. 1A. It has been known that there is an isomer of N3 dye. The structural formula of the isomer is shown in FIG. 1B. Both dyes have four carboxyl groups and adsorb strongly to a silica packing material which is generally used in normal-phase chromatography.

(Sample Preparation Method)

Commercially available N3 dye is dissolved in methanol at a concentration of 1 mg/mL. The solvent dissolving a sample dye is not limited to methanol. The solvent is preferably the same as a mobile phase in fractionation conditions in a preparative liquid chromatograph which is in the latter part, or the same as a mobile phase in the analysis conditions, or preferably contains some of the components in the mobile phase. When the solvent (sample solvent) dissolving the dye is not compatible with the mobile phase, the dye solution and the mobile phase are not mixed together, which may hinder normal separation. Since a large quantity of the dye solution is introduced during the preparative purification, the use of a solvent with higher eluent power (generally, a solvent with higher polarity) than the mobile phase as a sample solvent causes separation of the sample not with the mobile phase but with the sample solvent, which may hinder normal separation. To prevent this, the sample solvent to be used desirably contains the same components as in the mobile phase or some of the components in the mobile phase. Furthermore, it is desirable that the polarity of the sample solvent not be higher than that of the mobile phase.

As an apparatus for separating N3 dye, for example, a liquid chromatograph can be used, and a high-speed liquid chromatograph is preferred. A liquid chromatograph used in an example is shown schematically in FIG. 2.

Figure 2:
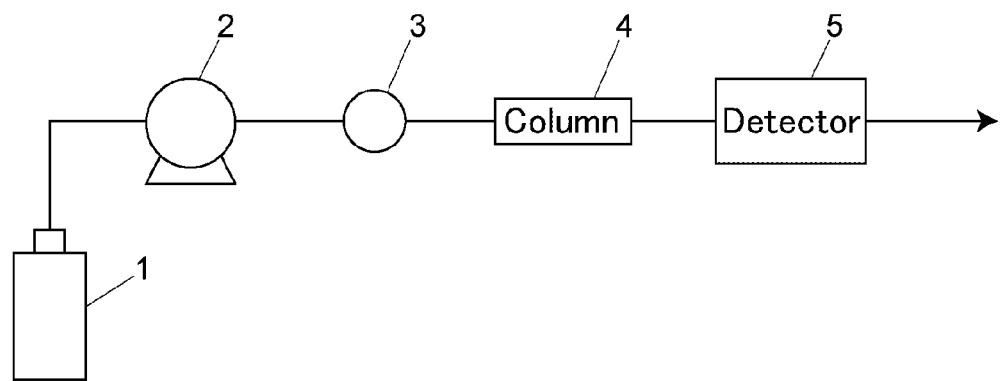
FIG. 2 is a schematic configuration diagram showing a high-speed liquid chromatograph with which an analysis method of an example was performed.

In FIG. 2, a liquid delivery pump 2 is provided to supply an eluent from an eluent reservoir 1 to a separation column 4 which separates sample components; and a sample introducing device 3 which introduces a sample is provided along an eluent passage to a separation column 4. In order to detect components which are separated by the separation column 4 and eluted, a detector 5 is provided along the passage connected to the outlet of the separation column 4. An eluate which has passed through the detector 5 is discharged to a drain.

(Separation Conditions)
Sample: Solution of N3 in methanol
Injection volume: 1 µL
Column: LiChrocart 125-4 LiChrosphere 100 Diol (5 µm)
Eluent: Dichloromethane/methanol/trifluoroacetic acid=90/10/1
Flow rate: 1 mL/min
Detection wavelength: 548 nm In the column used, a silica base material, which is a packing material, is modified with a modifying group having a hydroxyl group. An example of the modifying group is shown in the following structural formula.

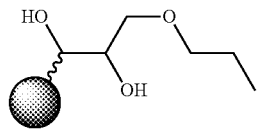

The adsorption of the dye to the column packing material is suppressed by the modifying group. The eluent contains trifluoroacetic acid. Trifluoroacetic acid competitively inhibits adsorption of the carboxyl groups of the dye to the column packing material, thereby suppressing adsorption of the dye to the column packing material. In this way, the effect of suppressing adsorption of the dye to the column packing material is controlled to achieve high separation of the dye.

Figure 3:
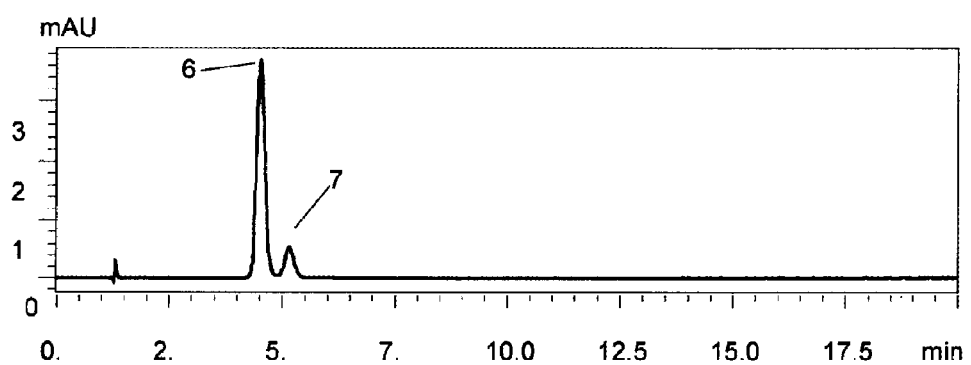
FIG. 3 is a chromatograph showing the analysis result of N3 dye in the example.

The chromatogram obtained by separation using the apparatus in FIG. 2 under the above separation conditions is shown in FIG. 3. The peak indicated by a reference numeral 6 in FIG. 3 is N3 dye shown in FIG. 1A; and the peak indicated by a reference numeral 7 is the isomer of N3 dye shown in FIG. 1B. This shows that the present invention can separate N3 dye from the isomer thereof. If separated N3 dye is recovered, the present invention can increase the purity of N3 dye as preparative purification.

Figure 4:
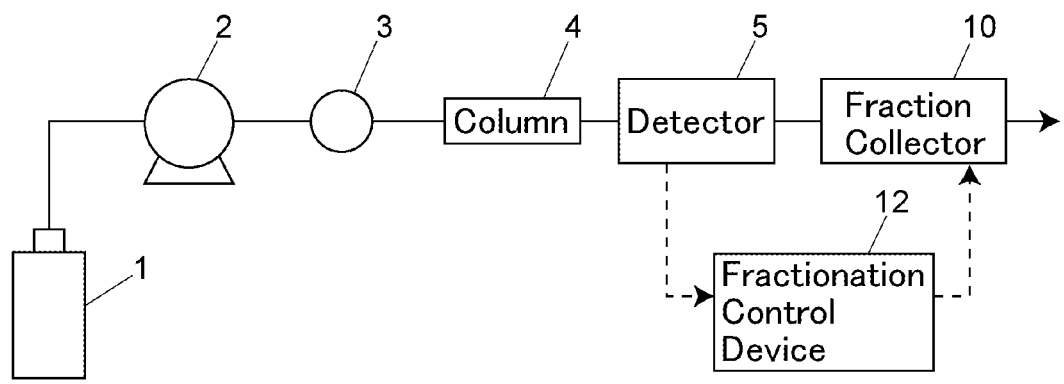
FIG. 4 is a schematic configuration diagram showing a preparative liquid chromatograph in another example.

For preparative purification, a preparative liquid chromatograph is used. An example of a preparative liquid chromatograph is shown in FIG. 4. In the preparative liquid chromatograph, a high-speed liquid chromatograph is provided with a fractionation device. The preparative liquid chromatograph includes: a separation column 4; a mobile phase container 1; a liquid delivery pump 2 which delivers a mobile phase stored in the mobile phase container 1 to the separation column 4; an injector 3 which introduces a sample into a mobile phase passage to the separation column 4; a detector 5 which detects sample components from the separation column 4; and a fractionation device. The fractionation device includes: a fraction collector 10 in a fractionation mechanism part, the fraction collector 10 collecting in fraction containers eluted sample components that have passed through the detector 5; and a fractionation control device 12 which controls operation of the fraction collector 10 based on the detection signals of the detector 5.

The fractionation control device 12 can be incorporated and realized in a control device composed of a computer only for the preparative liquid chromatograph, in which the computer performs operation of the preparative liquid chromatograph and data processing. The fractionation control device 12 can be also separated from the control device and realizable with a CPU or a general-purpose personal computer which is only for the fractionation device.

The fraction collector 10 includes a switching valve and test tubes as fraction containers.

A sample is introduced into the passage from the injector 3, delivered to the separation column 4 through the mobile phase, separated, and eluted. When the detector 5 is an optical detector, for example, a chromatogram obtained by absorbance or fluorescence at a specified wavelength is monitored, and the fractionation control device 12 controls valve switching of the fraction collector 10 based on the signals detected with the detector 5 at a specified wavelength.

Since the dye targeted for the present invention has high photosensitivity, the fractionation is preferably performing under the shaded condition in order to prevent the recovered dye from being deteriorated by light. As a method for shading, for example, employed can be a method for darkening the fraction containers and its surroundings in the fraction collector 10; or providing a trap column for solvent displacement and solvent removal, instead of the fraction containers in the fraction collector 10 in order to recover the separated dye, and trapping the separated dye on the trap column.

Although only N3 dye is tested as a dye for dye-sensitized solar cells in the example, other dyes for dye-sensitized solar cells also have similar polarity to the N3 dye and accordingly the present invention can be applied to other dyes in the same way.

DESCRIPTION OF REFERENCE SIGNS

1: Mobile Phase Container
2: Liquid Delivery Pump
3: Injector
4: Separation Column
5: Detector
10: Fraction Collector
12: Fractionation Control Device

The invention claimed is:
1. An analysis method for analyzing a sample, the method comprising the steps of:
(A) providing a sample solution dissolved in an organic solvent, the sample solution containing a dye for dye-sensitized solar cells;
(B) separating the sample solution by water-free normal-phase liquid chromatography; and
(C) detecting separated components,
wherein the dye is a metal complex having one or more aromatic heterocyclic ligands, and
wherein the water-free normal-phase liquid chromatography is an analysis method involving:
(B1) using a separation column filled with a column packing material which is prepared by modifying a base material with a polar modifying group, and
(B2) using as an eluent a polar organic solvent containing an acid.
2. The analysis method according to claim 1, wherein the normal-phase liquid chromatography is performed with a high-speed liquid chromatograph.
3. The analysis method according to claim 1, wherein the modifying group of the column packing material is/are one or more selected from the group consisting of a hydroxyl group, a cyano group, and an amino group.

4. The analysis method according to claim 1, wherein the acid contained in the eluent is/are one or more selected from the group consisting of acetic acid, formic acid, trifluoroacetic acid, and salts thereof.

5. The analysis method according to claim 1, further comprising the step of recovering a target dye based on a detection result, after the detection step (C), for preparative purification of the dye.

6. The analysis method according to claim 1, wherein the aromatic heterocyclic ligand is a polypyridyl derivative.

7. The analysis method according to claim 1, wherein the aromatic heterocyclic ligand is a porphyrin derivative.

* * * * *